United States Patent [19]

Brownlee

[11] Patent Number: 4,898,160

[45] Date of Patent: Feb. 6, 1990

[54] SURGICAL CAST VENTING DEVICE

[75] Inventor: Merrel Brownlee, Lowellville, Ohio

[73] Assignee: Alliance Group Inc., Youngstown, Ohio

[21] Appl. No.: 328,283

[22] Filed: Mar. 24, 1989

[51] Int. Cl.$^4$ .............................................. A61F 5/04
[52] U.S. Cl. ................................................. 128/91 R
[58] Field of Search .................... 128/91 R, 83, 89, 90, 128/87 R, 87 A, 87 B, 87 C

[56] References Cited

U.S. PATENT DOCUMENTS

| | | | |
|---|---|---|---|
| 432,899 | 7/1890 | Reenstierna | 128/89 R |
| 3,116,731 | 1/1964 | Baxter | 128/91 R |
| 3,656,477 | 4/1972 | Thomas | 128/91 R |
| 3,998,220 | 12/1976 | Cleer, Jr. et al. | 128/91 R |
| 4,387,710 | 6/1983 | Beatty, III | 128/91 R |

Primary Examiner—Robert A. Hafer
Assistant Examiner—Lynda M. Cofsky
Attorney, Agent, or Firm—Harpman & Harpman

[57] ABSTRACT

A surgical cast venting device to provide effective ventilation of the body part confined within the cast. The device includes a multiple channeled flexible form adjacent the skin that adapt to the contour of the body part to which it is applied. An air flow path is established on the skin with connector means provided from an air source outside the cast enclosed venting device.

2 Claims, 2 Drawing Sheets

SURGICAL CAST VENTING DEVICE

BACKGROUND OF THE INVENTION

1. Technical Field

This device relates to the ventilation of surgical casts used to immobilize a human or animal limb or the like for healing process of the bone or damaged tissue. It has been determined that by supplying air under the cast alleviates the typical irritation associated with the cast which is caused by the lack of air circulation to the skin in a free manner which is unavailable once the arm or limb has been encased in the cast material.

2. Description of Prior Art

Prior Art devices of this type have relied on a variety of different structures and methods in an attempt to supply ventilation to the skin under a cast, see for example U.S. Pat. No. 3,116,731, U.S. Pat. No. 3,656,477, U.S. Pat. No. 3,998,220 and U.S. Pat. No. 4,387,710.

In U.S. Pat. No. 3,116,731 a cast ventilating arrangement is disclosed wherein a vent body is positioned within the cast and supplies air to a continuous layer of cotton padding wrapped around the body portion under the cast. The vent has multiple openings in a convex cone extending from a pair of oppositely disposed support and positioning tabs.

U.S. Pat. No. 3,656,477 is directed to an orthopedic cast which has a series of air vents which communicate with a stockingetts placed on the limb over which a cast is applied. An apertured sponge plug is positioned in each of the vents to protect the skin from foreign material infiltration.

In U.S. Pat. No. 3,998,220 a cast ventilating apparatus is shown having a generally disk shaped base with an upstanding tubular portion. A plurality of elongated spacers within the base define air passageways that communicate with a stockingett to provide ventilation at one point thereto.

U.S. Pat. No. 4,387,710 is directed to a ventilated cast structure that uses a compact fibrous layer of material positioned against the skin of the body part. Conditioned air is supplied under positive pressure to a stockingett embedded within the cast body. The air passes through the fibrous layer around the limb and vents outwardly at the terminal ends of the cast.

SUMMARY OF THE INVENTION

The invention comprises an expendable ventilating device for a surgical cast that provides a regulated equal distribution of air onto the skin of the patient under the cast. The device utilizes spaced parallel venting channels interconnected to one another and a air supply. The ventilating device has a flexible panel-like configuration that can be cut along prescribed lines for a variety of sizes for corresponding areas of use without disrupting the airflow characteristics of the device.

DESCRIPTIONS OF THE DRAWINGS

DESCRIPTION OF THE PREFERRED EMBODIMENT

Figure 1:
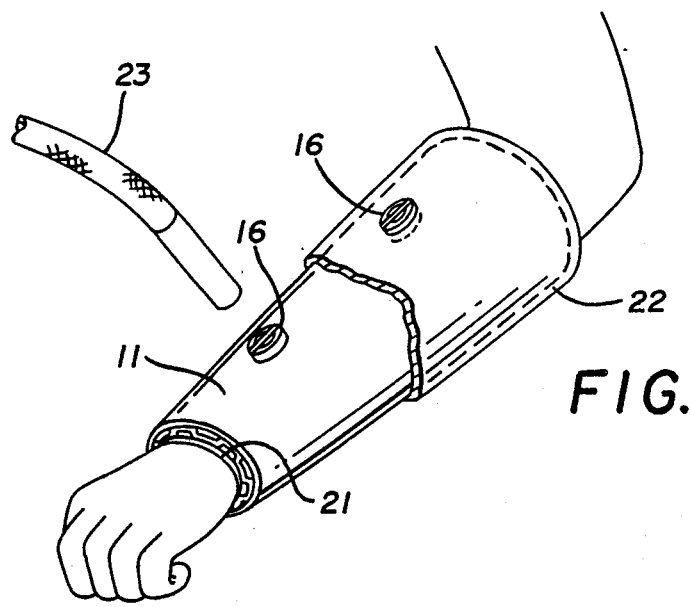
FIG. 1 is a perspective view of the cast ventilating device on a patient with a portion of the cast broken away.
Figure 2:
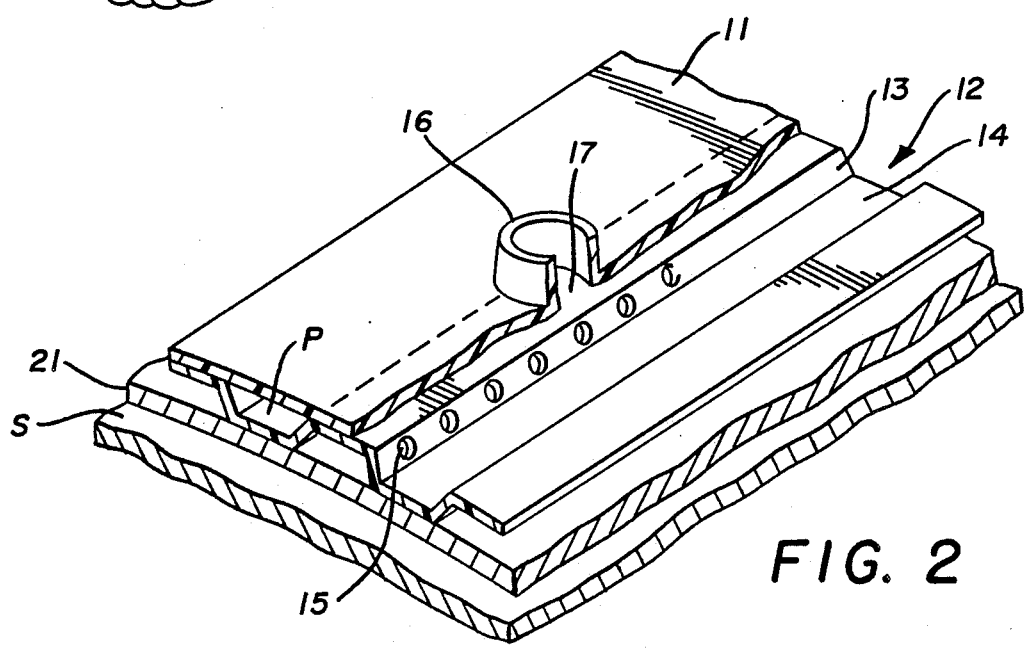
FIG. 2 is an enlarged perspective portion of the cast ventilating device positioned on the skin of a user.
Figure 4:
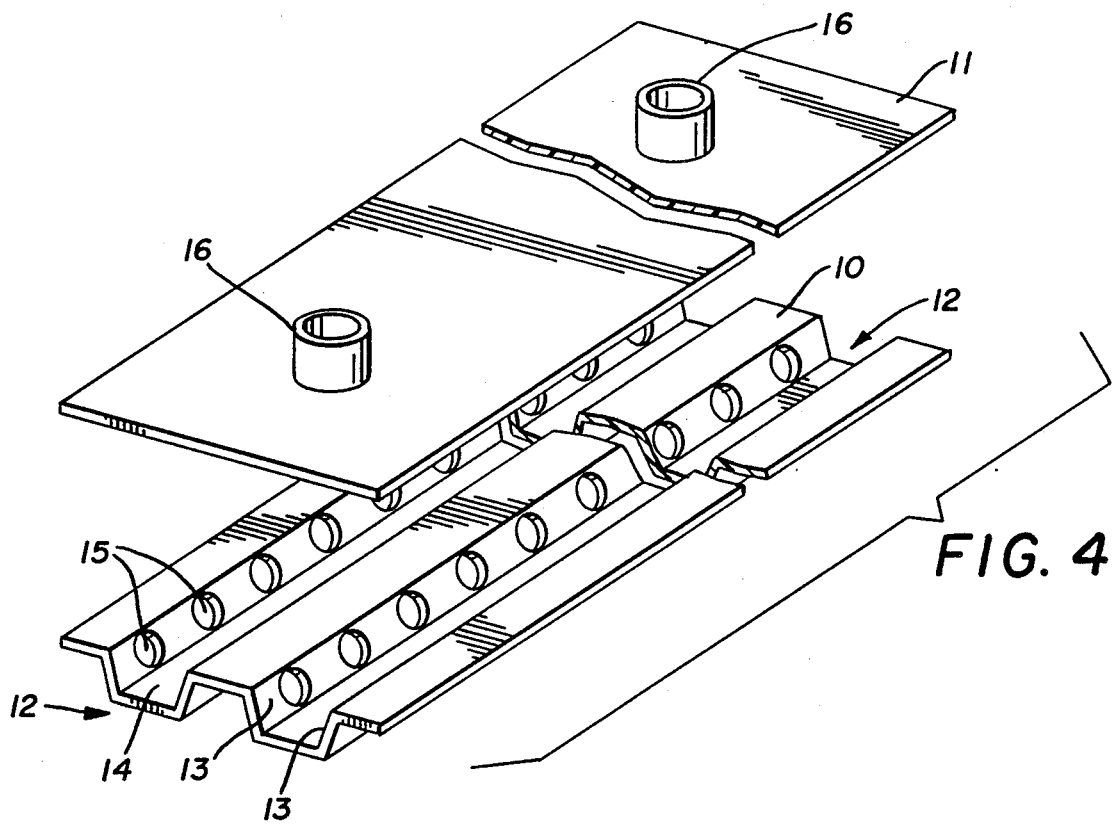
FIG. 4 is a perspective exploded view of the cast ventilating device.

A surgical cast ventilating device can be seen in FIGS. 1, 2, 4, and 5 of the drawings comprising a base portion 10 and a closure portion 11. The base porton 10 is formed with a plurality of parallel opposite facing elongated channel configurations 12 therein. The channel configurations 12 are preferrably formed by injection molding plastic resin material. The channel configurations 12 have oppositely disposed spaced upstanding angular side walls 13 interconnected continuously by generally horizontally disposed members 14. Each of the elongated channel configurations 12 share said side walls 13 with the respective alternate channel configurations 12 facing in opposite directions, as best seen in FIGS. 2 and 4 of the drawings.

Figure 5:
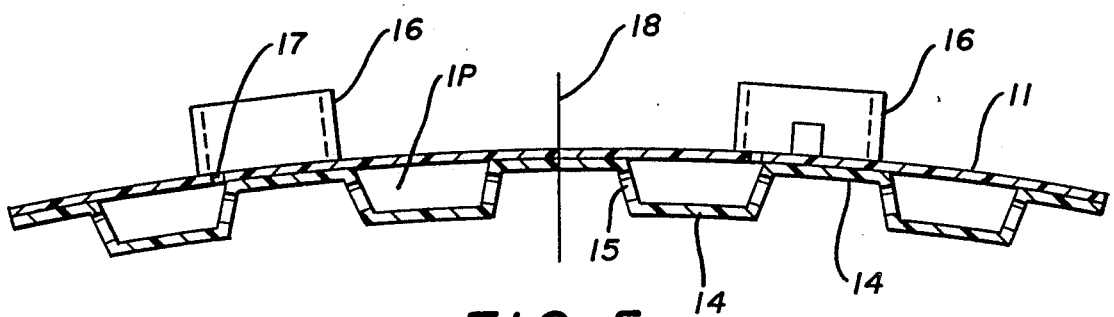
FIG. 5 is a cross-sectional view of an extended portion of the device shown in FIGS. 2 and 4 of the drawings.

A plurality of longitudinally spaced apertures 15 are formed in each of the sidewalls 13 along the entire length of each of said side walls 13 allowing free communication between adjacent channel configurations 12. The closure portion 11 is flat thin plastic resin material conforming to the overall surface size and dimension of said base portion 10. At least one tubular upstanding vent 16 is formed in said closure portion 11 defining an air supply aperture 17. Referring now to FIGS. 2 and 5 of the drawings, the closure portion 11 is permanently sealed to the respective engaging surfaces of said base portion 10 defining the spaced elongated air passageways P and the channel configurations 12 facing said closure portion 11. The vents 16 are positioned so as to engage at least a portion of the air passageways P so that air can be supplied thereto as will be described hereinafter.

In FIG. 5 of the drawings it will be seen that the venting device can be manufactured in a wide configuration containing many air passageways P and multiple vent portions 16 so that a selection of size and air passageways P can be made by cutting the sealed respective base portion and closure portion 11 on the line indicated at 18.

In use, the surgical cast venting device is wrapped around the body portion, such as an arm A, which is to be placed in a cast over a cast stockingette 21 which is normally placed on the body portion before the cast is applied. Once the surgical cast venting device is positioned, it is held in place temporarily and a conventional cast 22 is applied thereover. The vents 16 extend above the surface of the finished cast 22, see FIG. 1 of the drawing. An air supply line 23 can be connected to the vent opening 16 allowing air under positive pressure to flow into the air passageways P which are interconnected via said spaced apertures 15 as hereinbefore described. The finished cast 22 will effectively close the respective free ends of the air passageways P forcing the supplied air to circulate around the surgical cast venting device and vent through the stockingette 21 on the patient.

Figure 3:
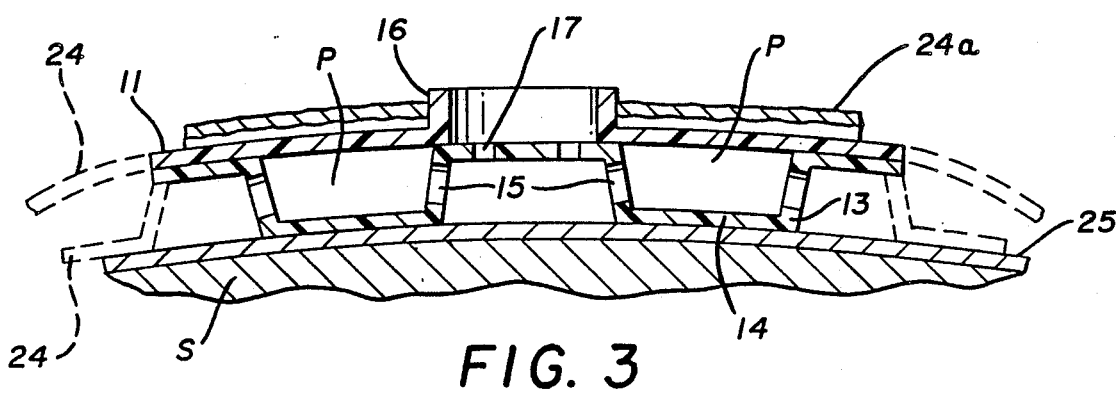
FIG. 3 is a cross-sectional view of an alternate form of the invention.

Referring now to FIG. 3 of the drawings, an alternate form of the invention is shown which is to be used on large wounds where a cast is not needed, but ventilation of the skin surfaces is wherein both the closure portion 11 and the base portion 10 extend outwardly beyond the respective ends (shown in broken lines) to form a tapered edge configurations 24. The vent 16 has been repositioned to be directly over one skin engaging air passage P to afford better general air movement as would sometimes be needed in this type of application. Bandages (dressing) 24A extend over the closure portion 11, as best seen in FIG. 3 of the drawings and a skin engaging dressing 25 is directly connected with the respective registration areas as noted above.

Thus it will be seen that a lightweight, flexible, disposable surgical cast venting device has been illustrated and described which allows for positive ventilation of the patient's limb under the cast or in an alternate form of the invention supplies a positive venting apparatus for large wounds and the like. It will be apparent to those skilled in the art that various changes and modifications may be made therein without departing from the spirit of the invention, therefore I claim:

I claim:

1. A surgical cast venting device for positioning on a layer of stockingnette on a patient's limb under a cast, said device comprising a flexible base portion, several parallel elongated channels in said base portion arranged in side by side relation in alternating upward and downward face directions, a flexible closure engaging said upward facing channels so as to form air passageways therein, an air supply opening in said closure communicating with said parallel elongated channels, apertures interconnecting said parallel elongated channels said channels having common side walls and said apertures being in said common side walls, whereby air supplied said opening flows through said parallel elongated channels for delivery thereby to said layer of stockingnette on said patient's limb.

2. The surgical cast venting device of claim 1 wherein said closure is shaped to include at least one elongated flexible flange extending beyond said parallel elongated channels said elongated flexible flange being deformable toward said stockingnette under said cast.

* * * * *